US006544962B1

(12) United States Patent
Jones et al.

(10) Patent No.: US 6,544,962 B1
(45) Date of Patent: Apr. 8, 2003

(54) METHODS FOR TREATING CELLULAR PROLIFERATIVE DISORDERS

(75) Inventors: Richard E. Jones, Palo Alto, CA (US); Ning Y. Yu, Saratoga, CA (US)

(73) Assignee: Matrix Pharmaceutical, Inc.

( * ) Notice: Subject to any disclaimer, the term of this patent is extended or adjusted under 35 U.S.C. 154(b) by 88 days.

(21) Appl. No.: 09/714,776

(22) Filed: Nov. 15, 2000

Related U.S. Application Data

(60) Provisional application No. 60/245,535, filed on Nov. 2, 2000.

(51) Int. Cl.⁷ .................................................. A61K 31/70
(52) U.S. Cl. .......................................... 514/49; 514/492
(58) Field of Search ........................... 514/49, 497, 449

(56) References Cited

U.S. PATENT DOCUMENTS 5,595,979 A * 1/1997 Snyder ........................ 514/49
5,665,711 A * 9/1997 Sakai et al. .................... 514/49

FOREIGN PATENT DOCUMENTS

EP          664 708          8/1998

OTHER PUBLICATIONS

Sukara, et al., Synergistic antitumor activity of (E)–2'–fluoromethylene–2'–deoxycytidine (FMdC, MDL 101,731), an inhibitor of ribonucleotide reductase in combination with S phase specific drugs. Proccedings of the 83th Annual Meeting of the American Association for Cancer Research, (Mar. 1992) vol. 33, No. 3088, pp. 517.

Woessner, Richard D., et al., FMdC Antineoplasic Ribonucleotide–Diphosphate Reductase Inhibitor, Drugs of the Future (1999), 24(5): pp. 502–510.

* cited by examiner

Primary Examiner—James H. Reamer
(74) Attorney, Agent, or Firm—Robert P. Blackburn; Steven W. Collier

(57) ABSTRACT

Methods of treating cancer by administration of FMdC followed by administration of a platinate are disclosed.

28 Claims, 1 Drawing Sheet

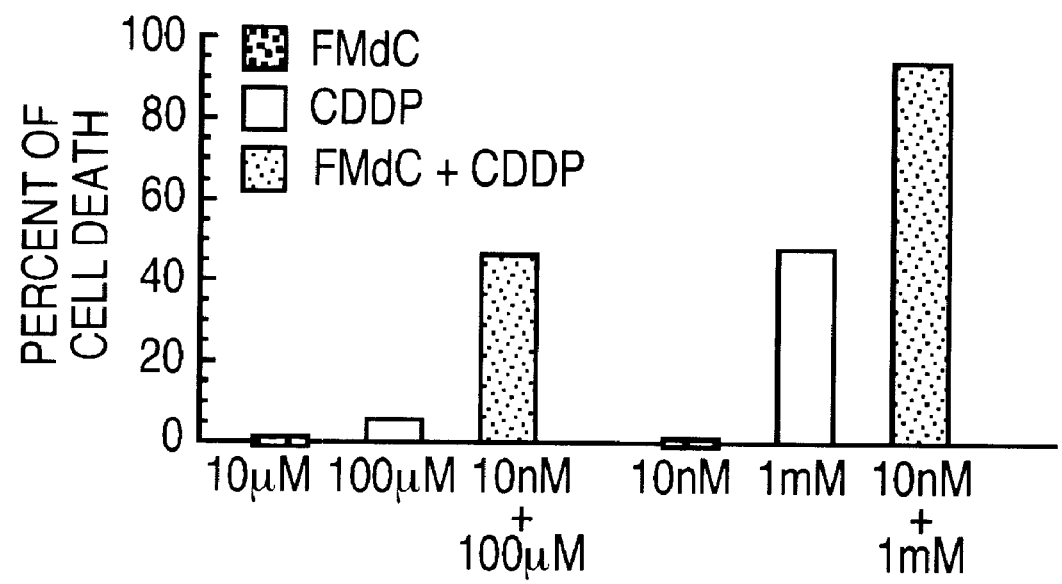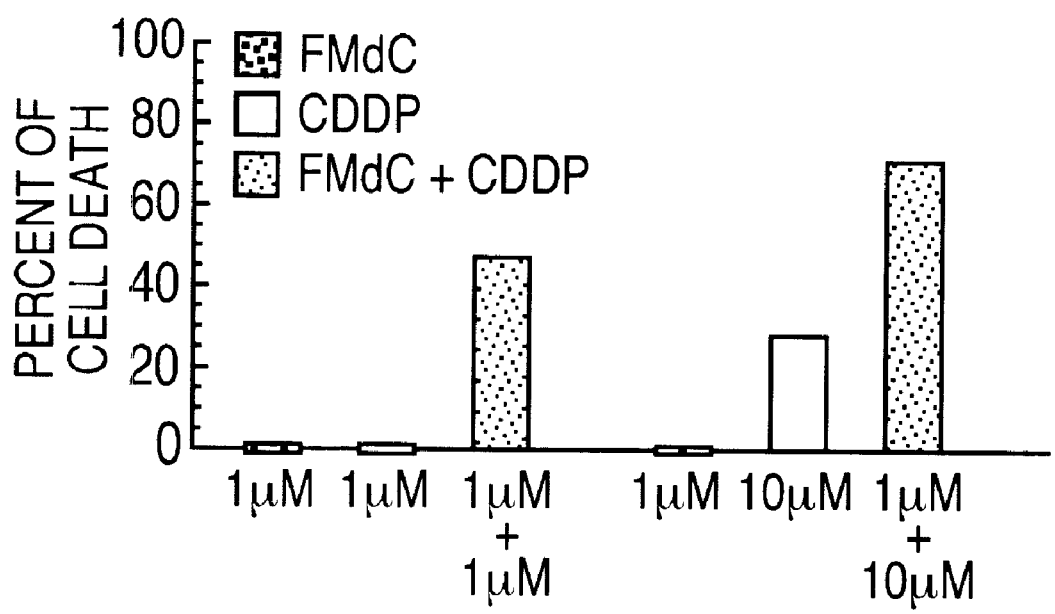

METHODS FOR TREATING CELLULAR PROLIFERATIVE DISORDERS

CROSS REFERENCE TO RELATED APPLICATIONS

This application claims the benefit of U.S. Provisional Application Serial Number 60/245,535, filed Nov. 2, 2000, as attorney docket number 018240-031.

BACKGROUND OF THE INVENTION

1. Field of the Invention

This invention relates to the treatment of cellular proliferative disorders, e.g., cancer, by administering to a patient (E)-2'-fluoromethylene-2'-deoxycytidine ("fluoromethylenedeoxycytidine" or "FMdC"), in combination with administering to the patient a platinate drug to increase the effectiveness of the treatment.

2. References

The following references are cited herein and are incorporated by reference in their entirety:

1. Sunkara et al., Synergistic antitumor activity of (E)-2'-fluoromethylene-2'-deoxycytidine (FMdC, MDL 101, 731), an inhibitor of ribonucleotide reductase in combination with S phase specific drugs. Proceedings of the 83 Annual Meeting of the American Association for Cancer Research, (March 1992) vol. 33, no. 3088, page 517;
2. Sunkara, European Patent EP 0 664 708;
3. Woessner, Richard D. et al., FMdC Antineoplastic Ribonucleotide-Diphosphate Reductase Inhibitor, Drugs of the Future (1999) 24(5):502–510.

STATE OF THE ART (E)-2'-deoxy-2'-(fluoromethylene)cytidine ("FMdC"), a nucleoside analogue of deoxycytidine, is an anti-tumor agent. It has been shown to have effective cytotoxic activity against a wide variety of cancer tumor cells and has potent anti-tumor activity in a large number of xenograft models, including breast, prostate, lung, colon, stomach, pancreas, ovary, brain and hematopoietic cancers.

Once taken in by a cell, the FMdC prodrug is phosphorylated to yield FMdC di- and triphosphates. FMdC diphosphate irreversibly inhibits ribonucleotide reductase, resulting in a reduction in deoxyribonucleotide triphosphate ("dNTP") pools. FMdC triphosphate competes with deoxycytidine triphosphate ("dCTP") for incorporation into DNA, resulting in DNA chain termination and cell death. The combination of these two activities results in self-potentiation of the drug.

It has been demonstrated that FMdC as a single agent has potent in vitro cytotoxic activity against a wide variety of tumor cells as noted above. However, FMdC is effective (cytotoxic) only in cells undergoing active DNA synthesis. Thus, the greatest utility for FMdC in treating cancer may be in combination with agents that induce DNA synthesis by inducing DNA repair, e.g., DNA-damaging agents.

Platinates are cytotoxic drugs containing a core atom of platinum, including cisplatin, carboplatin and others. They are DNA-damaging agents and are used in the treatment of cancer because of their efficacy. Cisplatin (cis-diamminedichloroplatinum; cis-Pt(NH$_3$)$_2$Cl$_2$; "CDDP") is the best known example of this class of cytotoxic agents and has been used for many years in the treatment of solid tumors. However, the toxicity of these agents continues to be a major concern.

Accordingly, a need exists for an improved therapy for the treatment of cancer both to increase effectiveness and to decrease toxicity. It has been discovered that a treatment reginen of FMdC combined with a platinate (such as cisplatin as an example of the class) is effective in the treatment of cellular proliferative disorders (cancer).

SUMMARY OF THE INVENTION

This invention is directed to methods for treating cellular proliferative disorders. In particular, it is directed to a method for treating a cellular proliferative disorder in a patient by administering to the patient an effective amount of (E)-2'-deoxy-2'-(fluoromethylene)cytidine and administering to the patient an effective amount of a platinate, wherein the amounts of (E)-2'-deoxy-2'-(fluoromethylene)cytidine and platinate are selected to provide effective cellular proliferative disorder treatment.

In one embodiment, it is directed to a method for treating a cellular proliferative disorder in a patient comprising administering to the patient an effective amount of (E)-2'-deoxy-2'-(fluoromethylene)cytidine (FMdC); waiting a predetermined period; and administering to the patient an effective amount of a platinate. The amounts of (E)-2'-deoxy-2'-(fluoromethylene)cytidine and the platinate are selected to provide effective cellular proliferative disorder treatment.

In another embodiment, it is directed to a method for treating a cellular proliferative disorder in a patient comprising administering to the patient an effective amount of (E)-2'-deoxy-2'-(fluoromethylene)cytidine (FMdC); waiting until at least a portion of the FMdC has been taken up by a cell and phosphorlyated; and administering to the patient an effective amount of a platinate. The amounts of (E)-2'-deoxy-2'-(fluoromethylene)cytidine and cisplatin are selected to provide effective cellular proliferative disorder treatment.

In yet another embodiment, it is directed to a method for treating a cellular proliferative disorder in a patient comprising administering to the patient an effective amount of (E)-2'-deoxy-2'-(fluoromethylene)cytidine (FMdC); and administering to the patient an effective amount of cisplatin. The amounts of (E)-2'-deoxy-2'-(fluoromethylene)cytidine and cisplatin are selected to provide effective cellular proliferative disorder treatment.

The methods of this invention are used in the treatment of cellular proliferative disorders including lung cancer, breast cancer, prostate cancer, colon cancer, stomach cancer, pancreatic cancer, ovarian cancer, brain cancer, hematopoietic cancers, esophageal carcinoma, renal cell carcinoma, bladder cancer, head and neck cancer, leukemias, and sarcomas such as cholangiosarcoma and esophageal sarcoma.

The platinate is selected from cisplatin, carboplatin, oxaliplatin, ormaplatin, iproplatin, enloplatin, nedaplatin, ZD0473 (cis-amminedichloro(2-chloropyridine)platinum (II)), BBR3464 and the like. A preferred platinate is cisplatin.

Preferably, the FMdC is administered prior to the administration of the platinate. A predetermined period is selected between the administration of FMdC and the platinate. The predetermined time is 15 minutes to 24 hours. Preferably, it is from about 1 to 8 hours and more preferably it is about 4 hours.

In the methods of this invention, FMdC is administered in an amount from about 2 mg/m$^2$ to about 800 mg/m$^2$ body surface of the patient and the platinate, such as cisplatin, is administered from about 10 mg/m$^2$ to about 150 mg/m$^2$ body surface of the patient. FMdC may be administered either parenterally or orally and the platinate may be administered either parenterally or orally.

BRIEF DESCRIPTION OF THE DRAWINGS

FIGS. 1A and 1B are graphs depicting the results of in vitro assays conducted in Example 1.

DESCRIPTION OF THE INVENTION

This invention is directed to methods for treating cellular proliferative disorders. In particular, it is directed to a method for treating cellular proliferative disorders in a patient by administering to the patient an effective amount of (E)-2'-deoxy-2'-(fluoromethylene)cytidine in combination with an effective amount of a DNA-damaging platinate. A preferred embodiment is a method for treating cellular proliferative disorders in a patient by administering to the patient an effective amount of (E)-2'-deoxy-2'-(fluoromethylene)cytidine, waiting a predetermined period, and administering an effective amount of a DNA damaging agent such as cisplatin.

Prior to the discussion of this invention, the following terms are defined:

The term "cellular proliferative disorder" refers to cancer, including breast, prostate, lung, colon, stomach, pancreatic, ovarian, brain and hematopoietic cancers, esophageal carcinoma, renal cell carcinoma, bladder cancer, head and neck cancer, leukemias, and sarcomas such as cholangiosarcoma and esophageal sarcoma. In particular, this includes non-small-cell lung cancer (NSCLC), colorectal cancer, leukemia and lymphoma.

The term "cellular proliferative disorder treating amount" refers to the dose or amount of drug needed in order to realize a decrease in tie number of cancer cells, reduce tumor size or eliminate the cancerous cells. These include, but are not limited to lung cancer, breast cancer, prostate cancer, colon cancer, stomach cancer, pancreatic cancer, ovarian cancer, brain cancer, hematopoietic cancers, esophageal carcinoma, renal cell carcinoma, bladder cancer, head and neck cancer, leukemias, and sarcoma s such as cholangiosarcoma and esophageal sarcoma. Additional examples of such tumors include, but are not limited to, adenocarcinomas, glioblastomas (and other brain thumors), cervical, colorectal, endometrial, gastric, liver, lung (small cell and non-small cell), lymphomas (including non-Hodgkin's, Burkitt's, diffuse large cell, follicular and diffuse Hodgkin's), melanoma (metastatic), neuroblastoma, osteogenic sarcoma, retinoblastoma, soft tissue sarcomas, testicular and other tumors which respond to chemotherapy.

"(E)-2'-deoxy-2'-(fluoromethylene)cytidine," also referred to as "FMdC," is a nucleoside analogue of deoxycytidine, and is an antitumor agent. After intracellular uptake, FMdC is phosphorylated to FMdC di- and triphosphates. It is believed that FMdC diphosphate irreversibly inhibits ribonucleotide reductase, resulting in a reduction in dNTP pools. Further, FMdC triphosphate competes with dCTP for in corporation into DNA, resulting in DNA chain termination and cell death. The combination of these two activities results in self-potentiation of the drug.

"Platinates" refer to cytotoxic drugs that contain platinum as a central atom. Examples of platinates include cisplatin, carboplatin, oxaliplatin, ormaplatin, iproplatin, enloplatin, nedaplatin, ZD0473 (cis-amminedichloro(2-chloropyridine) platinum (II)), BBR3464 and the like.

"Cisplatin" refers to cis-diamminedichloroplatinum (cis-Pt(NH$_3$)$_2$Cl$_2$ or "CDDP"). It is an anti-tumor drug and has been shown to be effective in treating many types of tumors, such as, but not limited to, head and neck cancers, lung, ovarian and testicular cancers.

The term "DNA-damaging agent" refers to a compound which damages DNA. DNA-damaging agents include cytotoxic platinates described above such as cisplatin, carboplatin, oxaliplatin and other platinum based drugs.

The term "predetermined time" or "predetermined period" refers to a preselected amount of time between the administration of FMdC and the DNA-damaging agent such as cisplatin. This is selected to maximize the combined cytotoxic effect of FMdC and the DNA-damaging agent on the cellular proliferative disorder. This time is also selected to allow for cellular uptake of FMdC and phosphorylation of FMdC to a biologically active molecule. As noted above, once taken in by a cell, the FMdC prodrug is phosphorylated to yield FMdC di- and triphosphates. FMdC diphosphate irreversibly inhibits ribonucleotide reductase, resulting in a reduction in deoxyribonucleotide triphosphate ("dNTP") pools. FMdC triphosphate competes with deoxycytidine triphosphate ("dCTP") for incorporation into DNA, resulting in DNA chain termination and cell death.

"Effective amount" refers to an amount of active compound, such as FMdC and/or platinate, which, when administered to the patient, is effective to treat the cellular proliferative disorder. This includes a reduction of symptoms of the disease, a shrinking of tumor size, death of the cells of the proliferative disorder (cancer), and any other indicators known in the art which show the treatment of the cellular proliferative disorder.

The methods of the present invention are useful in the treatment of mammalian cancer tumors, including human cancer tumors, particularly solid tumors. Thus, the methods of the present invention can be used to treat cancer tumors, including experimentally-induced cancer tumors, in any type of mammal including humans, commonly used laboratory animals such as rats, mice, rabbits and dogs, primates such as monkeys, and horses, cats and other animals.

Treatment regimens of this invention are directed to the administration of a combination of FMdC and a platinates. A preferred embodiment is the administration of FMdC, waiting a predetermined period and then administering the platinate. Preferably, the platinate is cisplatin.

The predetermined period is selected to maximize the efficacy of the combined administration of FMdC and the platinate. The time period is selected to allow cellular uptake of FMdC and phosphorlyation by cellular mechanisms once inside the cell. In particular, the predetermined period is from about 10 minutes to 24 hours. More preferably, the predetermined period is between about one hour and eight hours. Most preferably, the predetermined period is about four hours.

The amount of FMdC and cisplatin (or other platinate) administered to the patient for treatment ranges from about 2 mg/m$^2$ to about 800 mg/m$^2$ of body surface, depending upon the dose schedule, of FMdC, and about 10 mg/m$^2$ to about 150 mg/m$^2$ of body surface, depending on the dose schedule, of cisplatin or other platinate. The dose determination is well within the skill of the physician administering the treatment and will generally be determined based upon the body weight, gender, age, health, body surface area and other factors considered by a skilled physician.

Preferably, the FMdC and cisplatin (or other platinate) are administered parenterally in a solution. Alternatively, FMdC may be administered intraarterially, intravenously, intraperitoneally, orally, etc., in certain situations in some cancers. For instance, lyophilized FMdC may be reconstituted to an appropriate desired concentration with sterile saline solution as directed by the manufacturer. The platinate may also be administered by other routes, e.g., intraarterial, intraperitoneal, oral, etc. For example, the cisplatin may be prepared to an appropriate desired concentration by reconstitution of lyophilized cisplatin with sterile water according to manufacturers instructions (Cisplatin for Injection, David Bull Laboratories). Cisplatin may also be prepared from cisplatin solutions (Cisplatin Injection, Bristol). A pharmaceutically acceptable carrier may also be added to the solution of FMdC or cisplatin for administration to the patient.

Pharmaceutical Formulations

FMdC and the platinate, such as cisplatin, are usually administered in the form of pharmaceutical compositions. These drugs can be administered by a variety of routes including oral, transdermal, parenteral, subcutaneous, intravenous, intraarterial, intraperitoneal and intramuscular. These drugs can be effective as both injectable and oral compositions. The compositions used for administration are prepared in a manner well known in the pharmaceutical art.

This invention also includes pharmaceutical compositions which contain, as the active ingredient, FMdC and a platinate, such as cisplatin, with pharmaceutically acceptable carriers. In making the compositions used in this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, sterile injectable solutions, and sterile packaged powders.

In preparing a formulation, it may be necessary to mill the active ingredient to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methylparaben and propylparaben; sweetening agents; and flavoring agents. The compositions used in this invention can be formulated so as to provide quick, sustained or delayed release of the active ingredient after administration to the patient by employing procedures known in the art.

The compositions are preferably formulated in a unit dosage form, each dosage containing from about 1 to about 100 mg of FMdC per unit dosage, and about 5 to about 50 mg cisplatin or other platinate per unit dosage. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

It is understood that the dosage form of FMdC and the platinate (e.g., cisplatin) may be formulated as individual drug products. Alternatively, the FMdC and platinate may be formulated together in the same dosage form. The individually formulated drugs are appropriate for administration where there is a predetermined time between the administration of FMdC and the platinate, such as cisplatin.

Preferably, the active ingredient is employed at no more than about 20 weight percent of the pharmaceutical composition, more preferably no more than about 15 weight percent, with the balance being pharmaceutically inert carrier(s). However, FMdC and cisplatin may each be formulated as 100% active compound without the addition of excipients, such as in a lyophilized form.

The active ingredient is effective over a wide dosage range and is generally administered in a pharmaceutically effective amount. It will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredients of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can separated by enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the drugs used in this invention may be incorporated for administration orally include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

The liquid forms in which the drugs used in this invention may be used for parenteral administration include aqueous solutions, liposomal preparations, aqueous microemulsions, lipid solutions or suspensions, and the like.

EXAMPLES

The methods of this invention are exemplified below. Abbreviations used herein have their commonly accepted meaning unless otherwise noted.

| | | |
|---|---|---|
| mM | = | millimolar |
| μL | = | microliter |
| mL | = | milliliter |
| mg | = | milligram |
| kg | = | kilogram |
| min | = | minute |
| i.p. | = | intraperitoneally |

Example 1

The antiproliferative activity of FMdC in combination with cisplatin on growth inhibition in human carcinoma cell lines in vitro was studied using the following method.

Two lung carcinoma cell lines, A549 and Calu-6, (available through ATCC, Rockville, Md.), were cultured in F12K medium with 10% fetal bovine serum at an atmosphere of 5% $CO_2$ at 37° C. All cells were exposed to both FMdC and cisplatin in different concentrations for 72 hours.

Cell growth inhibition was determined by measuring the metabolic activity of cells using the MTT (tetrazolium salt) assay. For the MTT assays, the cells were seeded at $4 \times 10^3$ in 100 μL per well in a 96-well microtiter culture plate. The concentration of FMdC ranged from 10 nM to 100 μM and the concentration of cisplatin ranged from 1 μM to 10 mM. At the end of the treatment, tetrazolium salt (MTT) was added to each well and then solubilized. The microtiter plate was then measured (O.D. at 570 nm) using an ELISA plate reader. The 50% inhibitory concentrations ($IC_{50}$) values of FMdC and cisplatin as single agents and in combination were determined.

These results are summarized in graphic form in FIGS. 1A and 1B. It was shown that as single agents, FMdC and cisplatin were not effective on either cell line. However, the combination of FMdC and cisplatin resulted in cell death in both cell lines. When the concentration of cisplatin was increased, the percentage of cell death increased.

Example 2

This example evaluated the effect of FMdC in combination with cisplatin in a human non-small-cell lung cancer (NSCLC) xenograft model. This combination was compared to the administration of the combination of gemcitabine with cisplatin. Gemcitabine (Gemzar®, Eli Lilly and Company) is 2'-deoxy-2',2'-difluorocytidine (dFdC).

Xenogeneic NSCLC tumors of A549 cells (available through ATCC, Rockville, Md.) were induced by intradermal injection of approximately $5 \times 10^6$ cells into the flanks of female nu/nu mice. Two to three weeks after tumor cell inoculation, when the tumors were approximately 10 $mm^3$ in size, treatment with FMdC, gemcitabine or cisplatin solution was administered intraperitoneally (i.p.) in a volume of approximately 10 μL per gram of mouse body weight. Six to eight animals were used per treatment group.

The injectable solutions were prepared as follows: Lyophilized FMdC was reconstituted with sterile saline to a concentration of 2 or 20 mg/mL; gemcitabine was reconstituted with sterile saline to a concentration of 2 mg/mL; and cisplatin solution was prepared from lyophilized cisplatin (Cisplatin for Injection, David Bull Laboratories) by reconstitution with sterile water to a concentration of 0.4 or 0.6 mg/mL.

For this multiple treatment regimens, FMdC or gemcitabine was administered twice a week for two weeks at 20 mg/kg and cisplatin was administered once a week for two weeks at 4 mg/kg. FMdC was administered by injection 15 minutes prior to the administration of cisplatin.

Tumor growth and animal body weight were determined twice weekly for up to 30 days. Tumor volume quadrupling time (TVQT) was used as the study endpoint. Tumor growth delay (TGD) is the difference between TVQTs of a treated group and untreated control.

The results of this study are summarized below:

TABLE 1

Anti-tumor Activity of FMdC and Gemcitabine in Combination with CDDP: A549 Human NSCLC Xenografts, Multiple Dose

| Treatment Groups | Dosing Regimen | No. Animals | TVQT (days) (M ± SE) | TGD (days) (M ± SE) | Additivity Factor* |
|---|---|---|---|---|---|
| 1 Untreated Control | — | 7 | 16.8 ± 1.2 | — | — |
| 2 FMdC | 20 mg/kg Day 0, 3, 7, 10 | 7 | 19.8 ± 1.1 | 3.0 ± 1.6 | — |
| 3 Gemcitabine | 20 mg/kg Day 0, 3, 7, 10 | 7 | 18.7 ± 1.0 | 1.9 ± 1.6 | — |
| 4 CDDP | 4 mg/kg Day 0, 7 | 7 | 18.1 ± 0.9 | 1.3 ± 1.5 | — |
| 5 FMdC + CDDP | 20 mg/kg Day 0, 3, 7, 10; 4 mg/kg Day 0, 7 | 7 | 26.1 ± 0.9 | 9.3 ± 1.5 | 2.2 ± 1.2 |
| 6 Gemcitabine + CDDP | 20 mg/kg Day 0, 3, 7, 10; 4 mg/kg Day 0, 7 | 7 | 19.5 ± 1.6 | 2.7 ± 2.0 | 0.8 ± 0.8 |

*Additivity Factor = $TGD_{combination}/TGD_{DrugA} + TGD_{DrugB}$, < 1.0 subadditive; = 1.0 additive; > 1.0 supra-additive As can be seen from the above results, in a multiple treatment regimen, the combination of FMdC and cisplatin resulted in a more than additive effect in A549 NCSLC xenografts in nude mice. In contrast, the combination of gemcitabine with cisplatin was additive at best. In one group, one animal had no measurable tumor at the end of the 30-day study.

Example 3

This example evaluated the effect of FMdC in combination with cisplatin in two human non-small-cell lung cancer (NSCLC) xenograft models. This example examined the influence of the time interval between FMdC and cisplatin administration.

Xenogeneic NSCLC tumors of A549 cells or Calu-6 cells (available through ATCC, Rockville, Md.) were induced by intradermal injection of approximately $5 \times 10^6$ cells into the flanks of female nu/nu mice. Two to three weeks after tumor cell inoculation, when the tumors were approximately 10 $mm^3$ in size, treatment with FMdC and/or cisplatin solution was administered intraperitoneally (i.p.) in a volume of approximately 10 μL per gram of mouse body weight. Six to eight animals were used per treatment group.

The injectable solutions were prepared as follows: Lyophilized FMdC was reconstituted with sterile saline to a concentration of 2 or 20 mg/mL; was reconstituted with sterile saline to a concentration of 2 mg/mL; and cisplatin solution was prepared from lyophilized cisplatin (Cisplatin for Injection, David Bull Laboratories) by reconstitution with sterile water to a concentration of 0.4 or 0.6 mg/mL.

Tumor growth and animal body weight were determined twice weekly for up to 30 days. Tumor volume quadrupling time (TVQT) was used as the study endpoint. Tumor growth delay (TGD) is the difference between TVQTs of a treated group and untreated control.

The results of this study are summarized below:

TABLE 2

Influence of Time Interval Between FMdC and CDDP Administration on Anti-tumor Activity: A549 Human NSCLC Xenografts, Single Dose

| Treatment Groups | Drug Dose (mg/kg) | No. Animals | TVQT (days) (M ± SE) | TGD (days) (M ± SE) | Additivity * Factor |
|---|---|---|---|---|---|
| 1 Untreated Control | — | 6 | 14.2 ± 0.9 | — | — |
| 2 FMdC | 200 | 6 | 17.8 ± 1.0 | 3.6 ± 1.3 | — |
| 3 CDDP | 6 | 6 | 16.1 ± 1.8 | 1.9 ± 2.0 | — |
| 4 FMdC → 10 min → CDDP | 200/6 | 6 | 20.4 ± 2.3 | 6.2 ± 2.5 | 1.1 ± 0.7 |
| 5 FMdC → 4 h → CDDP | 200/6 | 6 | 25.4 ± 1.8 | 11.2 ± 2.0 | 2.0 ± 0.9 |
| 6 FMdC → 8 h → CDDP | 200/6 | 7 | 24.7 ± 1.1 | 10.5 ± 1.5 | 1.9 ± 0.9 |
| 7 FMdC → 24 h → CDDP | 200/6 | 6 | 21.7 ± 2.0 | 7.5 ± 2.2 | 1.4 ± 0.7 |

* Additivity Factor = $TGD_{combination}/TGD_{DrugA} + TGD_{DrugB}$, < 1.0 subadditive; = 1.0 additive; > 1.0 supra-additive

TABLE 3

Influence of Time Interval Between FMdC and CDDP Administration on Anti-tumor Activity: Calu-6 Human NSCLC Xenografts, Single Dose

| Treatment Groups | Drug Dose (mg/kg) | No. Animals | TVQT (days) (M ± SE) | TGD (days) (M ± SE) | Additivity Factor* |
|---|---|---|---|---|---|
| 1 Untreated Control | — | 8 | 9.3 ± 0.4 | — | — |
| 2 FMdC | 200 | 8 | 11.3 ± 0.4 | 2.0 ± 0.6 | — |
| 3 CDDP | 6 | 8 | 18.1 ± 1.5 | 8.8 ± 1.6 | — |
| 4 FMdC → 10 min → CDDP | 200/6 | 8 | 17.5 ± 2.2 | 8.3 ± 2.3 | 0.8 ± 0.3 |
| 5 FMdC → 4 h → CDDP | 200/6 | 8 | 23.7 ± 1.8 | 18.5 ± 3.5 | 1.7 ± 0.4 |
| 6 FMdC → 8 h → CDDP | 200/6 | 7 | 20.0 ± 2.5 | 11.9 ± 3.1 | 1.1 ± 0.3 |
| 7 FMdC → 24 h → CDDP | 200/6 | 8 | 20.6 ± 1.4 | 10.3 ± 1.5 | 1.0 ± 0.2 |

*Additivity Factor = $TGD_{combination}/TGD_{DrugA} + TGD_{DrugB}$, < 1.0 subadditive; = 1.0 additive; > 1.0 supra-additive In the single treatment regimen, administering FMdC four hours before cisplatin provided better enhancement of antitumor activity than did other dose timings in both A549 and Calu-6 NSCLC xenografts. Activity was approximately 1.7 to 2.0 fold greater than expected from additivity alone. The enhancement in antitumor efficacy by combining FMdC and cisplatin appears to be schedule and time dependent.

From the foregoing description, various modifications and changes in the compositions and method will occur to those skilled in the art. All such modifications coming within the scope of the appended claims are intended to be included therein.

What is claimed is:

1. A method for treating a cellular proliferative disorder in a patient comprising
   (a) administering first to the patient an effective amount of (E)-2'-deoxy-2'-(fluoromethylene)cytidine; and
   (b) administering 10 minutes to 24 hours after administration of (E)-2'-deoxy-2'-(fluoromethylene)cytidine to the patient an effective amount of a platinate to the patient;
      wherein the amounts of (E)-2'-deoxy-2'-(fluoromethylene)cytidine and platinate are selected to provide effective cellular proliferative disorder treatment.

2. A method for treating a cellular proliferative disorder in a patient comprising:
   (a) administering first to the patient an effective amount of (E)-2'-deoxy-2'-(fluoromethylene)cytidine;
   (b) waiting a predetermined period of at least 10 minutes up to 24 hours; and
   (c) administering to the patient an effective amount of a platinate;
      wherein the amounts of (E)-2'-deoxy-2'-(fluoromethylene)cytidine and the platinate are selected to provide effective cellular proliferative disorder treatment.

3. A method for treating a cellular proliferative disorder in a patient comprising:
   (a) administering to the patient an effective amount of (E)-2'-deoxy-2'-(fluoromethylene)cytidine;
   (b) waiting at least 10 minutes up to 24 hours until at least a portion of (E)-2'-deoxy-2'(fluoromethylene)cytidine is phosphorylated in vivo; and
   (c) administering to the patient an effective amount of a platinate; wherein the amounts of (E)-2'-deoxy-2'-(fluoromethylene)cytidine and platinate are selected to provide effective cellular proliferative disorder treatment.

4. The method of claim 2 wherein the predetermined period is between one hour and eight hours.

5. The method of claim 4 wherein the predetermined period is about four hours.

6. The method of claim 1, 2, or 3 wherein (E)-2'-deoxy-2'-(fluoromethylene)cytidine and platinate are in solutions suitable for administration to a patient.

7. The method of claim 6 wherein (E)-2'-deoxy-2'-(fluoromethylene)cytidine is administered by an administration route selected from the group consisting of parenterally and orally.

8. The method of claim 6 wherein the platinate is administered by an administration route selected from the group consisting of parenterally and orally.

9. The method of claim 1, 2 or 3 wherein the amount of (E)-2'-deoxy-2'-(fluoromethylene)cytidine is an amount of from about 2 mg/m$^2$ to about 800 mg/m$^2$ of the patient's body surface.

10. The method of claim 1, 2 or 3 wherein the amount of platinate is from about 10 mg/m$^2$ to about 150 mg/m$^2$ of the patient's body surface.

11. The method of claim 6 wherein the solution of (E)-2'-deoxy-2'-(fluoromethylene)cytidine further comprises a pharmaceutically acceptable excipient.

12. The method of claim 6 wherein the solution of platinate further comprises a pharmaceutically acceptable excipient.

13. The method of claim 1, 2 or 3 wherein the platinate is selected from the group consisting of cisplatin, carboplatin, oxaliplatin, ormaplatin, iproplatin, enloplatin, nedaplatin, ZD0473 (cis-amminedichloro(2-chloropyridine)platinum (II)) and BBR3464.

14. The method of claim 13 wherein the platinate is cisplatin.

15. A method for treating a cellular proliferative disorder in a patient comprising:
   (a) administering first to the patient an effective amount of (E)-2'-deoxy-2'-(fluoromethylene)cytidine; and
   (b) administering 10 minutes to 24 hours after administration of (E)-2'-deoxy-2'-(fluoromethylene)cytidine to the patient an effective amount of cisplatin to the patient;
      wherein the amounts of (E)-2'-deoxy-2'-(fluoromethylene)cytidine and cisplatin are selected to provide effective cellular proliferative disorder treatment.

16. The method of claim 15 wherein the predetermined period is between one hour and eight hours.

17. The method of claim 16 wherein the predetermined period is about four hours.

18. The method of claim 15 wherein (E)-2'-deoxy-2'-(fluoromethylene)cytidine and cisplatin are in solutions suitable for administration to a patient.

19. The method of claim 15 wherein (E)-2'-deoxy-2'-(fluoromethylene)cytidine is administered by an administration route selected from the group consisting of parenterally and orally.

20. The method of claim 15 wherein the cisplatin is administered by an administration route selected from the group consisting of parenterally and orally.

21. The method of claim 15 wherein the amount of (E)-2'-deoxy-2'-(fluoromethylene)cytidine is an amount of from about 2 mg/m$^2$ to about 800 mg/m$^2$ of the patient's body surface.

22. The method of claim 15 wherein the amount of cisplatin is from about 10 mg/m$^2$ to about 150 mg/m$^2$ of the patient's body surface.

23. The method of claim 18 wherein the solution of (E)-2'-deoxy-2'-(fluoromethylene)cytidine further comprises a pharmaceutically acceptable excipient.

24. The method of claim 18 wherein the solution of cisplatin further comprises a pharmaceutically acceptable excipient.

25. The method of claim 1, 2, 3 or 15 wherein the cellular proliferative disorder is selected from the group consisting of lung cancer, breast cancer, prostate cancer, colorectal cancer, stomach cancer, pancreatic cancer, ovarian cancer, brain cancer, hematopoietic cancers, esophageal carcinoma, renal cell carcinoma, bladder cancer, head and neck cancer, leukemias, and sarcomas such as cholangiosarcoma and esophageal sarcoma, esophageal carcinoma, renal cell carcinoma, bladder cancer, head and neck cancer and sarcomas.

26. The method of claim 25 wherein the lung cancer is non-small-cell lung cancer.

27. The method of claim 25 wherein the colorectal cancer is colon cancer.

28. The method of claim 25 wherein the hematopoietic cancer is selected from the group consisting of leukemias and lymphomas.

* * * * *